United States Patent [19]

Koch

[11] Patent Number: 5,684,046

[45] Date of Patent: Nov. 4, 1997

[54] HYDROGENATED NAPHTHALENES AND RELATED LTB$_4$ ANTAGONISTS

[75] Inventor: Kevin Koch, Boulder, Colo.

[73] Assignee: Pfizer Inc, New York, N.Y.

[21] Appl. No.: 642,711

[22] Filed: May 3, 1996

Related U.S. Application Data

[62] Division of Ser. No. 295,827, Jan. 9, 1995, Pat. No. 5,552, 435.

[51] Int. Cl.$^6$ .................. C07D 215/233; C07C 33/34
[52] U.S. Cl. .................. 514/569; 546/153; 546/155; 548/252; 560/315; 564/80; 564/84; 564/99; 568/808; 514/312; 514/381; 514/601; 514/604; 562/490
[58] Field of Search .................. 546/153, 155; 564/80; 560/315; 568/808; 548/252; 514/312, 601, 604, 381, 569

*Primary Examiner*—Johann Richter
*Assistant Examiner*—Laura L. Stockton
*Attorney, Agent, or Firm*—Peter C. Richardson; Paul H. Ginsburg; Gezina Holtrust

[57] ABSTRACT

Described herein are Benzopyran and other benzo-fused leukotriene B$_4$ antagonists have the formula

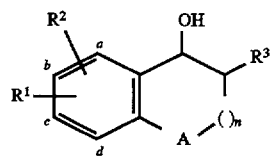

wherein R$^1$ is a phenyl or substituted phenyl group, and A, n, R$^2$ and R$^3$ are as defined herein.

13 Claims, No Drawings

HYDROGENATED NAPHTHALENES AND RELATED LTB$_4$ ANTAGONISTS

This application is a division of application Ser. No. 08/295,827, filed on Jan. 9, 1995, now U.S. Pat. No. 5,552,435.

This invention relates to novel benzopyran and other benzo-fused leukotriene B$_4$ (LTB$_4$) antagonists to pharmaceutical compositions containing such compounds, and to a method of using such compounds as LTB$_4$ antagonists.

The compounds of this invention inhibit the action of LTB$_4$, and are therefore useful in the treatment of LTB$_4$ induced illnesses such as inflammatory disorders including rheumatoid arthritis, osteoarthritis, inflammatory bowel disease, psoriasis and other skin disorders such as eczema, erythma, pruritis and acne, stroke and other forms of reperfusion injury, graft rejection, autoimmune diseases, asthma and other conditions where marked neutrophil infiltration occurs.

LTB$_4$, antagonists are disclosed in European patent publications 276 064 and 292 977 which refer to diphenylethers, benzophenones, and other compounds containing two phenyl groups, and 7-(3-alkoxy-4-alkanoyl-phenoxy)alkoxy benzopyran derivatives, respectively.

According to the invention, it was found that the following compounds of formula I have LTB$_4$, antagonistic properties:

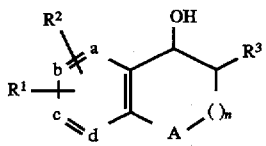

wherein

A is O, CH$_2$, S, NH, or N(C$_1$–C$_6$ alkyl); n is 0, 1 or 2; R$^1$ is a substituent at position b or c of the formula

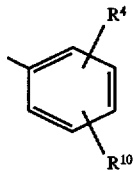

R$^2$, R$^8$, R$^9$ and R$^{10}$ are hydrogen or each independently are one or any two of the following fluoro, chloro, C$_1$–C$_6$ alkyl, C$_1$–C$_6$ alkoxy, C$_1$–C$_4$ perfluoroalkyl, C$_1$–C$_4$ perfluoroalkoxy, C$_1$–C$_6$ alkylthio, C$_1$–C$_6$ alkylsulfinyl, or C$_1$–C$_6$ alkylsulfonyl; R$^3$ is —(CH$_2$)$_q$CHR$^{11}$R$^{12}$, —(CH$_2$)$_q$R$^{12}$, —O(CH$_2$)$_p$CHR$^{11}$R$^{12}$, or —(CH$_2$)$_p$R$^{12}$, wherein p is 0, 1 or 2 and q is 0, 1, 2, or 3; R$^4$ is carboxy, tetrazolyl or R$^{13}$SO$_2$NHCO; R$^{11}$ is hydrogen, C$_1$–C$_6$ alkyl or R$^6$-substituted phenyl wherein R$^8$ is as defined above; R$^{12}$ and R$^{13}$ are hydrogen or each independently are C$_1$–C$_6$ alkyl or C$_3$–C$_8$ cycloalkyl; or phenyl, thienyl, pyridyl, furyl, naphthyl, quinolyl, isoquinolyl, pyrimidinyl, or pyrazinyl, each of which is optionally substituted by phenyl, R$^9$, or R$^9$-substituted phenyl wherein R$^9$ is as defined above; and the salts and esters of those compounds of formula I containing a carboxy group, wherein the esters contain ester groups selected from the group consisting of C$_1$–C$_6$ alkyl, phenyl (C$_1$–C$_6$) alkyl, C$_3$–C$_7$ cycloalkyl, and phenyl and benzyl substituted by fluoro, chloro, C$_1$–C$_6$ alkyl or a C$_1$–C$_6$ alkoxy.

Preferred compounds of the invention are those of formula I wherein A is oxygen, those wherein n is 1, those wherein R$^1$ is a substituent at position c, those wherein R$^2$ is hydrogen or monofluoro, and those wherein R$^3$ is benzyl, 4-fluorobenzyl. 4-phenylbenzyl, 4-(4-fluorophenyl)benzyl, phenethyl or phenoxy, preferably benzyl or 4-phenylbenzyl.

More specific compounds of the formula I are those wherein A is oxygen, n is 1, and R$^1$ is a substituent at position c, and those wherein A is oxygen, n is 1, R$^1$ is a at position c and is 2-carboxyphenyl, 3-carboxyphenyl, 2-carboxy-3-fluorophenyl, 2-carboxy-4-fluorophenyl, 2-carboxy-5-fluorophenyl, 2-carboxy-6-fluorophenyl, 2-carboxy-5-trifluoromethylphenyl, 2-tetrazolyl-5-fluorophenyl, 2-carboxy-5-chlorophenyl, or 2-carboxy-5-methoxyphenyl, R$^2$ is hydrogen or monofluoro and R$^3$ is benzyl, 4-fluorobenzyl, 4-phenylbenzyl, 4-(4-fluorophenyl)benzyl, phenethyl or phenoxy.

Specific compounds are those wherein A is oxygen, n is 1, R$^2$ is hydrogen, R$^3$ is benzyl, 4-fluorobenzyl, 4-phenylbenzyl, 4-(4-fluorophenyl)benzyl, phenethyl or phenoxy, and R$^1$ is at position c and is 2-carboxyphenyl, 3-carboxyphenyl, 2-carboxy-3-fluorophenyl, 2-carboxy-4-fluorophenyl, 2-carboxy-5-fluorophenyl, 2-carboxy-6-fluorophenyl ,2-carboxy-5-trifluoromethylphenyl,2-tetrazolyl-5-fluorophenyl,2-carboxy-5-chlorophenyl or 2-carboxy-5-methoxyphenyl, and those wherein in these specific compounds R$^3$ and the adjacent hydroxy group are trans.

The present invention also relates to a pharmaceutical composition for the treatment of LTB$_4$ induced illnesses comprising a compound of the formula I as defined above in an amount effective in the treatment of LTB$_4$ induced illnesses, and a pharmaceutically acceptable carrier.

This invention further comprises a method for the receptor binding inhibition of LTB$_4$ by administering to a subject in need of such inhibition a compound of formula I as defined above.

The invention further includes a process for the preparation of an intermediate compound of the formula

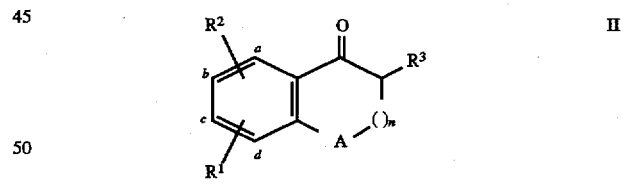

wherein A, n, R$^2$ and R$^3$ are as defined above with reference to formula I and R$^1$ is a substituent at position b or c of the formula

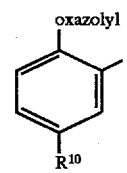

wherein R$^{10}$ is as defined above with reference to formula I, by reacting a compound of the formula

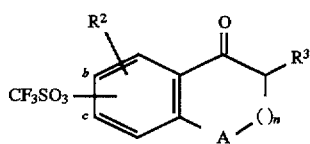

wherein $R^2$, $R^3$, A and n are as defined above with reference to formula I and the $CF_3SO_3$ group is at position b or c with a compound of the formula

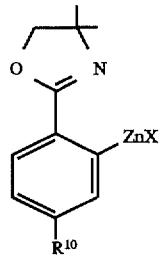

wherein X is chloro, bromo or iodo and $R^{10}$ is as defined above, which is prepared in situ by reaction of a compound of the formula.

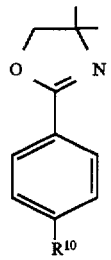

wherein $R^{10}$ is as defined above, with n-butyllithium and then $ZnX_2$ wherein X is as defined above.

The term "$C_1$-$C_6$ alkyl" whenever used in the disclosure herein such as in the definitions of $R^1$ to $R^{14}$ denotes saturated monovalent straight or branched aliphatic hydrocarbon radicals having one to six carbon atoms, such as methyl, ethyl, propyl, t-butyl, hexyl, etc. Similarly, the terms $C_3$-$C_7$ cycloalkyl and $C_3$-$C_8$ cycloalkyl denote a cycloalkyl group having from three to seven or eight carbon atoms, respectively, such as cyclopropyl, cyclohexyl, cyclooctyl, etc.

When A is oxygen and n is 1 in a compound of formula I, the compound may be described either as a 3,4-dihydrobenzopyran or a chromane.

The compounds of the invention have two asymmetric carbon atoms indicated by asterisks in the following formula:

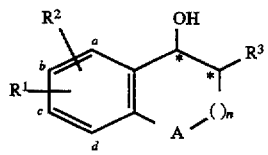

The stereoisomers may be designated with reference to R and S notation in accordance with standard nomenclature. When reference is made herein to S,R, or R,S, a single enantiomerically pure compound is meant, whereas S*, R* and R*, S* denote a racemic mixture. The invention includes the racemic mixtures and optical isomers of formula I.

According to a specific method of the invention, intermediate compounds of above formula II wherein $R^1$ is a substituent of the formula III, are prepared by reacting a compound of the formula IV as defined above with a compound of the formula V as defined above. This reaction generally proceeds in a solvent such as an ether solvent, e.g., tetrahydrofuran, diethyl ether, ethylene glycol dimethyl ether, 1,4-dioxane, and, preferably, tetrahydrofuran. The reaction is in the presence of a catalytic amount of a catalyst, particularly a palladium catalyst which is any palladium source which provides palladium (Pd°) under the reaction conditions, for instance tetrakistriphenyl phosphine palladium. The reaction is usually carded out at or about the reflux temperature of the solvent used, preferably at about 78° C. The reaction time is generally from about 1 to 24 hours, e.g., about 3 hours.

The compounds of the formula V are prepared in situ from a compound of the above formula VI by reaction thereof with n-butyllithium or sec.-butyllithium in hexanes at low temperatures of about –78° C., and then with $ZnX_2$ wherein X is iodo, bromo or chloro, generally at about 0 to about 78° C. for about one to four hours.

Ketones of the formula II wherein A, n, $R^4$, $R^2$ and $R^3$ are as defined with reference to formula I may be reduced to the corresponding hydroxyl compounds of formula I by reaction with sodium borohydride. Generally, the reduction is carded out in a solvent. Suitable solvents are lower alcohols having one to six carbon atoms, mixtures of lower alcohols with organic solvents such as tetrahydrofuran or dioxane, and mixtures of water-miscible lower alcohols or other water-miscible organic solvents with water. The solvent is preferably a lower alcohol such as methanol or ethanol. The reaction temperature generally ranges from about –78° C. to about 100° C., and usually from about 0° C. to about 25° C.

The reduction step results in a stereoisomeric mixture of the compounds of formula I having the following structures:

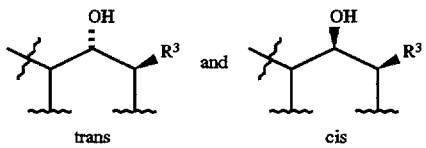

These cis and trans isomers may be separated by conventional column chromatography.

Resolution of the enantiomeric mixture resulting after separation of the cis and trans isomers may be accomplished by methods known in the art. In one method, a compound of the formula I wherein $R^1$ contains a carboxyl group (COOH) is reacted with a chiral base such as methylbenzylamine in a polar solvent such as ether to form diastereomeric salts which are separated and then convened into optically pure acids by treatment with an acid such as aqueous or methanolic hydrogen chloride. In another method, a compound of the formula I wherein $R^1$ contains an ester group is reacted with an optically active acid such as R-mandelic acid or N-t-butoxycarbonyl-D-tryptophan to form diastereomeric esters which are separated into optically pure esters, e.g. by chromatography. Removal of the resolving ester group and hydrolysis of the carboxylic acid ester group in $R^1$ is conveniently carried out with aqueous base such as an alkali metal hydroxide, e.g. sodium hydroxide, at temperatures ranging from about room temperature to the reflux or boiling temperature of the solvent or solvent mixture used. The reaction may be conducted in the presence of a co-solvent such as methanol, ethanol or tetrahydrofuran.

The compounds of formula I wherein $R^4$ is oxazolyl are converted into corresponding compounds of formula I wherein $R^4$ is carboxy by first reacting with methyl iodide in the optional presence of dimethylsulfoxide and then with a base such as aqueous sodium hydroxide.

The compounds of formula IV wherein $R^3$ is $(CH_2)_q CHR^{11}R^{12}$ or $(CH_2)_q R^{12}$ may be prepared according to reaction Scheme I from a compound of the formula VIII wherein A, n and $R^2$ are as defined with reference to formula I.

The compound of formula VIII is reacted with trifluoromethane sulfonic anhydride (also called triflic anhydride) in a suitable solvent such as methylene chloride in the presence of triethylamine to form the compound of formula IX.

The group $R^3$ when defined as $-(CH_2)_q CHR^{11}R^{12}$ or $-(CH_2)_q R^{12}$ may be introduced into the compound of formula IX by a two step procedure comprising reacting with an aldehyde of the formula $R^{11}R^{12}CH(CH_2)_{q-1}CHO$ or $R^{12}(CH_2)_{q-1}CHO$ to form a compound of the formulae XA or XB, respectively, and then hydrogenating. The reaction with the aldehyde is conducted in the presence of a pyrrolidine catalyst or with hydrochloric acid catalyst in acetic acid. The hydrogenation is carried out with hydrogen and a palladium catalyst in a conventional manner.

thereof with 20% potassium hydroxide and adding phenyldiacetoxy iodide.

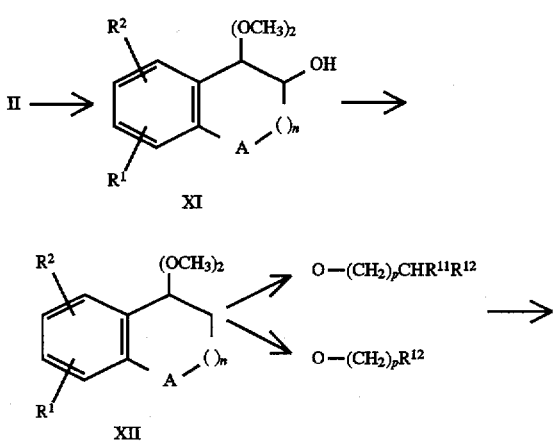

SCHEME I

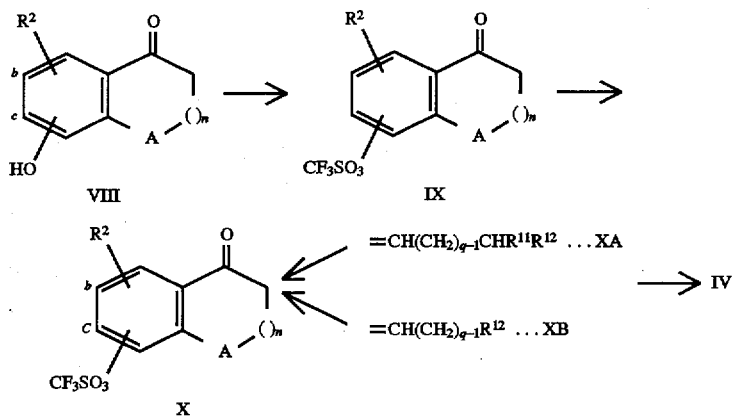

The compounds of formula VIII are generally commercially available. If not, they may be obtained by prior art methods. For instance, the compounds of formula VIII wherein A is oxygen and n is 1 may be obtained from $R^2$-substituted 2',4'-dihydroxy-3-chloropropiophenone (hereafter compound 1) by cyclization with sodium hydroxide. Compound 1 may be prepared from $R^2$-substituted resorcinol and 3-chloropropionic acid in the presence of an acid, preferably trifluoromethane sulfonic acid. The compounds of formula VIII wherein A is sulphur and n is 1 may similarly be obtained from $R^2$-substituted 4'-hydroxy-2'-sulfhydryl-3-chloro-propiophenone which may be obtained from $R^2$-substituted 3-hydroxythiophenol.

The compounds of formula VIII wherein n is 2 and A is O or S may similarly be obtained by reaction of $R^2$-substituted resorcinol or 3-hydroxythiophenol, respectively, and 4-chlorobutyric acid, and cyclization with sodium hydroxide.

The group $R^3$ when defined as $-O(CH_2)_p CHR^{11}R^{12}$ or $-O(CH_2)_p R^{12}$ may be introduced into the compound of formula VIII by the procedure outlined in Scheme II.

SCHEME II

The compounds of formula XI may be prepared from the compounds of formula II wherein $R^3$ is hydrogen by mixing -continued

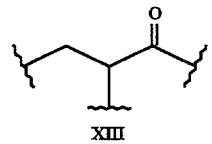

The compounds of formula XI when combined with $Br(CH_2)_p CHR^{11}R^{12}$ or $Br(CH_2)_p R^{12}$ form compounds of the formula XII which are converted to compounds of the formula XIII by hydrolysis with an acid such as hydrochloric acid. The compounds of formula XIII on reduction form compounds of the formula I. This reduction is carried out in a conventional manner with sodium borohydride in an alcohol solvent at ambient temperature.

The above compounds of formula IV may be converted into compounds of formula I wherein $R^1$ is as defined with reference to formula I and $R^4$ is carboxy in accordance with reaction Scheme III.

SCHEME III

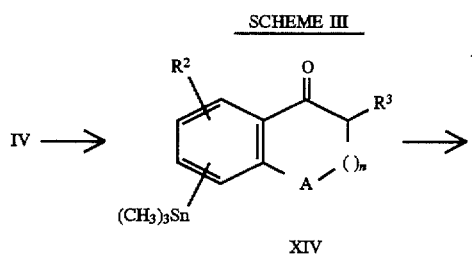

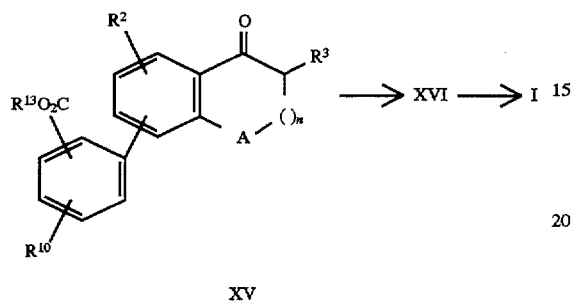

The compound of formula XIV is formed by reaction of the compound of formula IV with $(CH_3)_3SnSn(CH_3)_3$ and a palladium catalyst such as tetrakistriphenyl phosphine palladium $(Pd(PPh_3)_4)$, or bisbenzonitrile palladium chloride, in the presence of a phosphine ligand, such as triphenyl phosphine, in an amount of about 0.1 to about 5 molar equivalent per mole of substrate used. The compound of formula XIV is converted to a compound of formula XV by reaction with an ester-protected compound of the formula

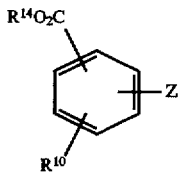

wherein $R^{10}$ is as defined with reference to formula I, $R^{14}$ is $C_1$–$C_6$ alkyl, phenyl or benzyl, and Z is iodo, bromo or $CF_3SO_3$. The coupling reaction proceeds in the presence of a palladium catalyst, such as tetrakistriphenyl phosphine palladium or bistriphenyl phosphine palladium chloride.

The ketone esters of the formula XV are first reduced to the corresponding hydroxyl compounds XVI (formula not shown) and then hydrolyzed to the corresponding acid of formula I. The reduction proceeds with sodium borohydride, as described before with reference to the reduction of the ketones of formula II. The hydrolysis to the acid may be carried out with an aqueous base such as an alkali metal hydroxide, e.g. sodium hydroxide, in the optional presence of a co-solvent such as methanol or ethanol at temperatures ranging from about room temperature to the reflux or boiling temperature of the solvent used.

The compounds of formula I wherein $R^1$ is

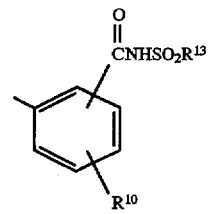

wherein $R^{10}$ and $R^{13}$ are as defined above with reference to formula I, may be obtained by reacting compounds of the formula I wherein $R^1$ is

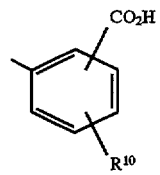

with a sulfonamide of the formula $R^{13}SO_2NH_2$ in the presence of a coupling agent such as 1,3-dicyclohexylcarbodiimide or 1-[3-(dimethylamino)propyl]-3-ethylcarbodiimide and in the presence of an organic base such as pyridine, dimethylaminopyridine, triethylamine, diisopropylethylamino or diazobicyclo[5.4.0]undec-7-ene. The reaction is carried out in a solvent such as tetrahydrofuran, diethyl ether, toluene, and chlorobenzene, at a temperature ranging from about room temperature to about the boiling point of the reaction solvent used.

The compounds of formula I wherein $R^4$ is tetrazolyl may be obtained from corresponding ester compounds of formula I wherein $R^4$ is a carboxyl $C_1$–$C_4$ alkyl ester group (—$CO_2$($C_1$–$C_4$)alkyl). The ester compound is first reacted with t-butyldimethylsilyl chloride in the presence of an organic base such as triethylamine or pyridine or, preferably, imidazole in a polar aprotic solvent, preferably dimethylformamide to protect the hydroxyl group as known in the art. The protected ester compound is reacted with ammonia and tri($C_1$–$C_6$)alkyl aluminum in xylene to replace the carboxyl ester group with cyano. The cyano group is reacted with trimethylstannyl azide in toluene at about 110° C. Conversion to tetrazolyl and removal of the silyl protecting group is attained by reaction with tetrabutylammonium fluoride in tetrahydrofuran to obtain the compounds of formula I wherein $R^4$ is tetrazolyl.

The salts of compounds of formula I containing a carboxy group may be prepared in a conventional manner by reaction with a base such as an alkali metal hydroxide, e.g., sodium hydroxide, or alkaline earth metal hydroxide, e.g., magnesium hydroxide. The esters of compounds I containing a carboxy group may be prepared in a conventional manner by reacting the acid group with a $C_1$–$C_6$ alcohol, such as ethanol, phenyl ($C_1$–$C_6$) alcohol, $C_3$–$C_7$ cycloalkanol, phenol or phenol substituted by one to three of fluoro, chloro, $C_1$–$C_6$ alkyl or $C_1$–$C_6$ alkoxy.

The compounds of the invention can be administered to humans for the treatment of $LTB_4$ induced illnesses by various routes including orally, parenterally and topically, and through the use of suppositories and enemas. On oral administration, dosage levels of about 0.5 to 1000 mg/day, advantageously about 5–500 mg/day may be given in a single dose or up to three divided doses. For intravenous administration, dosage levels are about 0.1–500 mg/day, advantageously about 1.0–100 mg/day. Intravenous administration can include a continuous drip. Variations will necessarily occur depending on the age, weight and condition of the subject being treated and the particular route of administration chosen as will be known to those skilled in the art.

The compounds of the invention may be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules either alone or in admixture with excipients, or in the form of elixirs or suspensions containing flavoring or coloring agents. They can be injected parenterally, for example, intramuscularly, intravenously or subcutaneously. For parenteral administration, they are best used in the form of a sterile aqueous solution which can contain other solutes, for example, enough salt or glucose to make the solution isotonic.

The $LIB_4$ activity of the compounds of the invention may be determined by comparing the ability of the compounds of the invention to compete with radiolabelled $LTB_4$ for specific $LTB_4$ receptor sites on guinea pig spleen membranes. Guinea pig spleen membranes were prepared as described by Cheng et al. (J. Pharmacology and Experimental Therapeutics 232:80, 1985). The $^3H$-$LTB_4$ binding assay was performed in 150 µl containing 50 mM Tris pH 7.3, 10 mM $MgCl_2$, 9% Methanol, 0.7 nM $^3H$-$LTB_4$ (NEN, approximately 200 Ci/mmol) and 0.33 mg/ml guinea pig spleen membranes. Unlabeled $LTB_4$ was added at a concentration 5 µM to determine non-specific binding. Experimental compounds were added at varying concentrations to evaluate their effects on $^3H$-$LTB_4$ binding. The reactions were incubated at 4° C. for 30 minutes. Membrane bound $^3H$-$LTB_4$ was collected by filtration through glass fiber filters and the amount bound was determined by scintillation counting. The IC50 value for an experimental compound is the concentration at which 50% of specific $^3H$-$LTB_4$ binding is inhibited.

The following Examples illustrate the preparation of the compounds of the invention.

EXAMPLE 1

A. 2',4'-Dihydroxy-3-chloropropiophenone

To a stirred mixture of resorcinol (200 g, 1.82 mol) and 3-chloropropionic acid (200 g, 1.84 mol) was added trifluoromethane sulfonic acid (1 kg) in one portion. The solution was heated slowly over 45 minutes to 80° C. then cooled to room temperature over 15 minutes and poured into chloroform (4.0 L). The organic portion was slowly poured into water (4.0 L) and the layers separated. The aqueous layer was extracted with chloroform (2×2.0 L). The combined organic layers were washed with brine, dried over sodium sulfate and filtered. Concentration in vacuo gave an orange semi-solid (244.1 g) which was used crude in the next step.

$^1$H-NMR (300 MHz, $CDCl_3$): 12.56 (1H,s), 7.63 (1H, d, J=7.6 Hz), 6.37–6.46 (2H, m), 3.92 (2H, t, J=6.3 Hz), 3.41 (2H, t, J=6.3 Hz).

B. 7-Hydroxybenzopyran-4-one

To a cooled (5° C.) solution of 2N sodium hydroxide (10.0 L) was added the compound of step A (244.1 g) in one portion. The solution was warmed to room temperature over 2 hours using a warm water bath then recooled to 5° C. and the pH adjusted to 2 with 6M sulfuric acid (1.2 L). The mixture was extracted with 3×3.0 L of ethyl acetate, washed with brine (1×2.0 L) dried over sodium sulfate and filtered. Concentration in vacuo gave a tan solid. Trituration with hexanes, and filtration afforded 173.7 g (58% yield) of the title compound. M.P. 136° C.–137° C.

C. 7-[(Trifluoromethylsulfonyl)oxy]-benzopyran-4-one

To a stirred solution of the compound of step B (173.7 g, 1.05 mole) in methylene chloride (3.0 L) at –78° C. was added triethylamine (320 g, 3.16 mole) and dimethylaminopyridine (2.5 g). After total dissolution, trifluoromethane sulfonic anhydride (327 g, 1.16 mole) was added dropwise over 20 minutes, the material was stirred for 30 minutes at –78° C., and then warmed to room temperature over 2 hours. The reaction mixture was poured into saturated ammonium chloride solution (2.5 L) and the layers separated. The aqueous layer was extracted with 2×2.0 L of methylene chloride. The combined organic fractions were washed with water (1×1.0 L), dried over magnesium sulfate and filtered. Concentration in vacuo gave a red oil. Chromatography over silica gel (1 kg) eluting with (8:1) hexane: ethyl acetate gave after solvent removal 211.1 g. (69% yield) of the title product. M.P. 43°–44° C.

D. 7-[(Trifluoromethylsulfonyl)oxy]-3-phenylmethyl-benzopyran-4-one

To a stirred solution of the product of Step C (27 g, 91.2 mmole) in 183 mL of methanol was added benzaldehyde (11.1 mL, 109 mmole) followed by pyrrolidine (9.1 mL, 109 mmole). The mixture was stirred at room temperature overnight, cooled to 0° C. and filtered. The solid was washed once with 50 mL of ice-cold methanol and then dried in vacuo; 35.2 g, (75% yield) of the title product was recovered. M.P. 133°–135° C.

$^1$H NMR (300 MHz) $CDCl_3$): 8.11 (1H, d, J=8.7 Hz), 7.91 (1H, bs), 7.40–7.51 (2H, m), 7.24–7.38 (3H, m), 6.97 (1 H, dd, J=8.7 Hz) 2.4 Hz), 6.91 (1H, d, J=2.4 Hz) 5.40 (1H, bs).

E. 7-[(Trifluoromethylsulfonyl)oxy]-3-phenylmethyl-benzopyran-4-one

To a solution of the compound of step D (26.6 g, 69.2 mmole) in 250 mL of ethyl acetate in a 500 mL Parr shaker flask was added 10% palladium on carbon catalyst (1.3 g). The mixture was hydrogenated at 40 psi until hydrogen uptake ceased after about 3 hours. The mixture was filtered through celite (a tradename for diatamaceous earth) to remove the palladium catalyst, and chromatographed over silica gel (hexane-ether); 25.1 g (94% yield) of the title product was obtained. M.P. 56°–58° C.

$^1$H NMR (300 MHz) $CDCl_3$): 8.01 (1H, d, J=8.5 Hz), 7.20–7.35 (5H, m), 6.981–6.96 (2H, m), 4.42 (1H, dd, J=11.6, 4.4 Hz, 4.22 (1H, dd, J=11.6 Hz) 8.7 Hz), 3.26 (1H, dd, J=14.0, 4.4 Hz), 2.90–3.05 (1H, m), 2.70 (1H, dd, J=14.0, 8.7 Hz).

F. 7-(Trimethylstannyl)-3-phenylmethyl-benzopyran-4-one

To a stirred solution the compound of step E (9.20 g, 25.0 mmole) in 200 mL of dioxane was added lithium chloride t3.20, 75.0 mmole), Pd($PPh_3$)$_4$ (1.15 g, 1.0 mmole), 3 crystals of butylated hydroxytoluene, and hexamethylditin (9.0 g, 27.5 mmole). The mixture was heated to reflux for 1.5 hours, cooled to room temperature and poured into 150 mL of saturated, aqueous ammonium chloride solution. The mixture was extracted with 3×50 mL of diethylether and the combined organic fractions were washed with brine, dried over sodium sulfate and filtered. Evaporation in vacuo gave a yellow semi solid which was chromatographed over silica gel (5:1 hexane: ether) to give 8.90 g (89% yield) of the title product. M.P. 84°–86° C.

$^1$H NMR (300 MHz, CDCl$_3$): 7.85 (1H, d, J=8.7 Hz), 7.18–7.37 (5H, m), 7.14 (1H, d, J=8.7 Hz), 7.11 (1H, s), 4.38 (1H, dd, J=11.6, 4.5 Hz), 4.17 (1H, dd, J=11.6 Hz, 8.4 Hz), 3.28 (1H, dd, J=14.0, 4.4 Hz), 2.84–2.95 (1H, m), 2.71 (1H, dd, J=14 Hz J=11.0 Hz), 0.31 (9H, s).

G. 7-(3-Carbomethoxyphenyl)-3-phenylmethyl-benzopyran-4-one

To a stirred solution of the compound of step F (7.0 g, 17.5 mmole) in dimethylformamide (DMF) (35 mL) was added Pd(PPh$_3$)$_2$Cl$_2$(490 mg, 0.7 mmole), 3 crystals of BHT and methyl-3-iodobenzoate (5.0 g, 19.1 mmole). The mixture was stirred at reflux for 1.5 hours, cooled to room temperature and poured into 150 mL of saturated aqueous ammonium chloride solution. The mixture was extracted with 3×150 mL of diethyl ether, and the combined extract was washed with 2×100 mL of water, and then brine. The solution was dried over sodium sulfate, filtered and evaporated in vacuo to afford a yellow oil. Chromatography over silica gel (4:1 hexane: ether elution) afforded 6.51 g of the title compound as a viscous oil.

$^1$H NMR (300 MHz, CDCl$_3$): 8.29 (1H, t, J=1.6 Hz), 8.06 (1H, dd, J=7.6, 1.6 Hz), 8.00 (1H, d, J=8.2 Hz), 7.79 (1H, dd, J=7.6 Hz, 1.6 Hz), 7.53 (1H, t, J=7.6 Hz), 7.22–7.36 (7H, m), 4.41 (1H, dd, J=11.6, 4.5 Hz), 4.21 (1H, dd, J=11.6, 8.5 Hz), 3.94 (3H, s), 3.31 (1H, dd, J=14.0, 4.4 hz), 2.91–2.99 (1H, m), 2.73 (1H, dd, J=14.0, 11.1 Hz)

H. 7-(3-Carbomethoxyphenyl)-4-hydroxy-3-phenylmethyl-benzopyran

To a stirred solution of the compound of step G (6.50 g, 17.5 mmole) in 35 mL of methanol at room temperature was added sodium borohydride (940 mg, 26.0 mmole) in one portion. The dark mixture was stirred at room temperature for 2 hours then poured into saturated aqueous ammonium chloride solution (75 mL) and extracted with 3×75 mL of diethyl ether. The combined extracts were washed with brine, dried over sodium sulfate, filtered and concentrated in vacuo to give an off-yellow oil. Chromatography on silica gel eluting with 4:1 hexane: ether afforded first 3.26 g of the cis ring isomer of the title compound, and then 1.98 g of the trans isomer of the title compound as viscous oils, total yield 81%.

Cis ring isomer: $^1$H NMR (300 MHz, CDCl$_3$): 8.26 (1H, t, J=1.7 Hz), 8.02 (1H, dt, J=7.8, 1.7 Hz), 7.76 (1H, dt, J=7.8, 1.7 Hz), 7.50 (H, t, J=7.8 Hz), 7.41 (1H, d, J=7.9 Hz), 7.31 (1H, d, 7.3 Hz), 7.14–7.25 (6H, m), 4.58 (1 Hz) J=7.2 Hz), 4.28 (1H, dd, J=9.1, 2.5 Hz), 4.03 (1H, dd, J=9.1, 5.4 Hz), 3.93 (3H, s), 2.78 (1H), 2.77 (1H, dd, J=13.7, 6.2 Hz), 2.58 (1H, dd, J=13.7, 9.1 Hz), 2.20–2.29 (1H, m), 1.83 (1H, d, J=7.2 Hz).

Trans ring isomer: $^1$H NMR (300 MHz, CDCl$_3$): 8.23 (1H, t, J=1.7 Hz), 7.98 (1H, dt, J=7.8 Hz), 7.74 (1H, t, J=7.8 Hz, 1.7 Hz), 7.48 (1H, t, J=7.8 Hz), 7.20–7.36 (6H, m), 7.15 (1H, dd, J=8.0, 1.8 Hz), 7.09 (1H, d, J=1.8 Hz), 4.56 (1H, dt, J=4.7, 3.8 Hz), 4.12–4.19 (2H, m), 3.92 (3H, s), 2.90 (1H, dd, J=13.6, 8.4 Hz), 2.70 (1H, dd, J=13.6, 7.2 Hz), 2.36–2.39 (1H, m), 1.75 (1H, d, J=4.7 Hz).

J. N-(α-Butoxycarbonyl-L-tryptophan-7[(3-carbomethoxyphenyl)-3-phenylmethyl]-chroman-4-yl]-ester To a stirred solution of the compound of step H (2.5 g, 6.7 mmole) in 70 ml of CH$_2$Cl$_2$ was added DMAP (897 mg., 7.34 mmole, 1.1 eq.), DCC (1.51 g, 7.34 mmole, 1.1 eq.) and N-t-Boc-L-tryptophan (2.4 g. 8.01 mmole, 1.2 eq.). The mixture was stirred at room temperature for 12 hours, filtered and washed with 1M HCl and brine. The organic layer was dried over MgSO$_4$, filtered and concentrated in vacuo. Chromatography (silica gel-3:1 cyclohexane:ether) afforded 860 mg of the less polar diastereomer (Rf=0.3) and 700 mg of the more polar moving diastereomer (Rf=0.2). The less polar product (3S, 4R): $^1$H-NMR (300 MHz, CDCl$_3$); 8.29 (1H, s), 8.03 (2H, d, J=7.8 Hz), 7.77–7.83 (2H, m), 7.52 (2H, t, J=7.6 Hz), 7.02–7.33 (5H, m), 6.64 (1H,s), 5.65 (1H, s), 5.06 (1H, d, J=8.4 Hz), 4.58–4.62 (1H, m), 3.95 (3H, s), 3.73–3.85 (2H, m) 3.18–3.28 (2H, m), 2.45–2.61 (2H, m), 2.09–2.15 (1H, brd s), 1.39 (9H, s). The more polar product (3R,4S); $^1$H-NMR (300 MHz. CDCl$_3$): 8.25 (1H, s), 8.01 (1H, d, J=7.8 Hz), 7.94 (1H, brd s), 7.74 (1H, d, J=8.2 Hz), 7.54 (1H, d, J=11.9 Hz), 7.48 (1H, t, J=7.8 Hz) 7.09–7.38 (H, m), 6.95 (1H, s), 5.61 (1H, s), 5.08 (1H, d, J=8.2 Hz, 4.55–4.60 (1H, m) 3.94 (3H, s), 3.73–3.76 (2H, m), 3.22–3.35 (2H, m), 2.42–2.60 (2H, m), 1.90–1.96 (1H, m), 1.39 (9H, s).

K. 3S,4R-7-(3-carboxyphenyl-4-hydroxy-3-phenylmethyl-2H-1-benzopyran

To a stirred solution of the less polar 4R,3S tryptophan ester of step L (840 mg, 1.08 mmole) in 10 mL of methanol was added 10 mL of 2M NaOH solution. The mixture was refluxed for 8 hours, cooled and acidified to a pH of 4 with 1M HCl. The cloudy emulsion was extracted with 3×20 mL of ethyl acetate, and the combined organic fractions were washed with brine and dried over MgSO$_4$. Filtration and solvent removal in vacuo afforded a yellow foam. Chromatography (silica gel-ethyl acetate: hexane: acetic acid -35:75:1) afforded 210 mg of product. $^1$H NMR. (300 MHz) CD$_3$CN): 8.22 (1H, t, 1.7 Hz), 7.97 (1H, dt, J=7.8, 1.7 Hz), 7.87 (1H, dt, J=7.8, 1.7 Hz), 7.55 (1H, t, J=7.8 Hz), 7.42 (1H, d, J=7.9 Hz), 7.15–7.36 (6H, m), 7.10 (1H, d, J=1.8 Hz), 4.44 (1H, d, J=4.9 Hz), 4.19 (1H, dd, J=9.1, 2.5 Hz), 3.97 (1H, dd, J=9.1, 5.4 Hz), 2.72 (1H, dd, J=13.7, 6.2 Hz), 2.51 (1H, dd, J=13.7, 9.1 Hz), 2.04–2.20 (3H, m). [α]$_D$=+11.1 at C=1.00 in methanol. M.P.=210°–212° C.

Saponification as above of the more polar 3R,4S tryptophan-ester (700 mg) gave the 3R,4S enantiomer, $^1$H-NMR (300 MHz, CD$_3$CN): 8.22 (1H, t, 1.7 Hz), 7.97 (1H, dt, J=7.8, 1.7 Hz), 7.87 (1H, dt, J=7.8, 1.7 Hz), 7.55 (1H, t, J=7.8 Hz), 7.42 (1H, d, J=7.9 Hz), 7.15–7.36 (6H, m), 7.10 (1H, d, J=1.8 Hz), 4.44 (1H, d, J=4.9 Hz), 4.19 (1H, dd, J=9.1, 2.5 Hz), 3.97 (1H, dd, J=9.1, 5.4 Hz), 2.72 (1H, dd, J=13.7, 6.2 Hz), 2.51 (1H, dd, J=13.7, 9.1 Hz), 2.04–2.20 (3H, m) [α]$_D$=−11.0 at c-1.01 in methanol. MP=209°–211° C.

L Trans 3-phenylmethyl-4-hydroxy-7-3-carboxyphenyl)-2H-1-benzopyran

Saponification as in step K of the trans ring isomer of step H gave the corresponding acid. $^1$H NMR (300 MHz) CD$_3$CN): 8.22 (1H, t, 1.7 Hz), 7.97 (1H, dt, J=7.8, 1.7 Hz), 7.87 (1H, dt, J=7.8, 1.7 Hz), 7.55 (1H, t, J=7.8 Hz), 7.42 (1H, d, J=7.9 Hz), 7.15–7.36 (6H, m), 7.10 (1H, d, J=1.8 Hz), 4.44 (1H, d, J=4.9 Hz), 4.19 (1H, dd, J=9.1, 2.5 Hz), 3.97 (1H, dd, J=9.1, 5.4 Hz), 2.72 (1H, dd, J=13.7, 6.2 Hz), 2.51 (1H, dd, J=13.7, 9.1 Hz), 2.04–2.20 (3H, m). M.P. 210°–212° C.

EXAMPLE 2

The following compounds in Table 1 were prepared by saponification in accordance with Example 1J. The melting points are in degrees Celsius.

TABLE 1

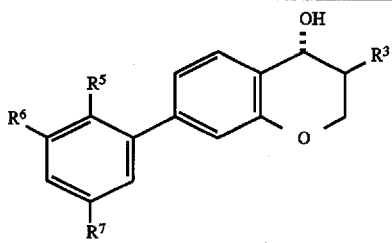

| R³ | R⁵ | R⁶ | R⁷ | Product |
|---|---|---|---|---|
| 4-phenylbenzyl | CO₂H | H | Cl | ¹H-NMR(300 MHz, DMSO$_{d6}$): 7.61–7.67(4H, m), 7.29–7.46 (6H, m), 6.93(1H, brd d, J=7.9Hz), 6.80(1H, br. s.), 4.38(1H, d, J=4.9Hz), 4.16 (1H, brd. d, J=11.0Hz), 4.02 (1H, dd, J=11.0, 5.6Hz), 2.96 (1H, m), 2.56(1H, m), 2.26 (1H, m). |
| benzyl | CO₂H | H | OCH₃ | (cis)¹H-NMR(300MHz, CDCl₃): 7.96(1H, d, J=8.7Hz), 7.24–7.38(5H, m), 7.16(1H, d, J=8.0Hz), 6.88 (1H, dd, J=8.7, 2.6Hz), 6.75–6.83(3H, m), 4.51(1H, d, J=2.9Hz), 4.06–4.15(2H, m), 3.84(3H, s), 2.90(1H, dd, J=13.6, 8.2Hz), 2.70(1H, dd, J=13.6, 7.2Hz), 2.27–2.39(1H, m). |
| benzyl | CO₂H | H | OCH₃ | (trans)¹H-NMR(300MHz, CDCl₃): 7.97(1H, d, J=8.7Hz), 7.17–7.31(6H, m), 6.85(2H, dt, J=14.3, 2.8Hz), 6.81–6.85(2H, m), 4.50(1H, d, J=4.1Hz), 4.20(1H, dd, J=11.2, 2.6Hz), 3.94(1H, dd, J=11.2, 4.8Hz), 3.86(3H, s), 2.76(1H, dd, J=13.8, 6.2Hz), 2.52(1H, dd, J=13.2, 9.4Hz), 2.22–2.30(1H, m). |
| benzyl | CO₂H | H | Cl | (cis)¹H-NMR(300MHz, CDCl₃): 7.83(1H, d, J=8.4Hz), 7.16–7.38(7H, m), 7.09(1H, d, J=89.1Hz), 6.72–6.84(2H, m), 4.47(1H, d, J=2.8Hz), 4.02–4.12(2H, m), 2.85(1H, dd, J=13.6, 8.1Hz), 2.62(1H, 13.6, 7.4Hz), 2.22–2.38(1H, m). |
| benzyl | CO₂H | H | Cl | (trans)¹H-NMR(300MHz, CDCl₃): 7.86(1H, d, J=8.3Hz), 7.14–7.42(8H, m), 6.76–6.84(2H, m), 4.48(1H, d, J=4.2Hz), 4.12(1H, dd, J=11.7, 2.6Hz), 3.92(1H, dd, J=11.7, 4.4Hz), 2.73(1H, dd, J=13.7, 6.1Hz), 2.50(1H, dd, J=13.7, 9.5Hz), 2.14–2.26(1H, m). |
| benzyl | CO₂H | H | H | (cis)¹H-NMR(300MHz, CDCl₃): 7.88(1H, dd, J=7.7, 1.2Hz), 7.49(1H, t, J=7.7Hz), 7.11–7.39(8H, m), 6.82–6.89(2H, m), 4.49(1H, d, J=3.0Hz), 4.06–4.11(2H, m), 2.87(1H, dd, J=13.6, 8.0Hz), 2.63(1H, dd, J=13.6, 7.4Hz), 2.28–2.38 (1H, m). |
| benzyl | CO₂H | H | H | (trans)¹H-NMR(300MHz, CDCl₃): 7.88(1H, dd, J=7.7, 1.2Hz), 7.52(1H, t, J=7.7Hz), 7.10–7.41(8H, m), 6.83–6.90 (2H, m), 4.43(1H, d, J=4.2Hz), 4.12(1H, dd, J=11.2, 2.9Hz), 3.88(1H, dd, J=11.2, 4.5Hz), 2.75(1H, dd, J=13.7, 5.8Hz), 2.51(1H, dd, J=13.7, 9.5Hz), 2.14–2.25(1H, m), MP 82–84°C. |
| 4-phenylbenzyl | CO₂H | H | F | ¹H-NMR(300MHz, DMSO d6): 7.8(1H, dd), 7.01–7.67 (3H, m), 7.29–7.46(6Hm), 6.93(HH, brd, d), 6.80(1H, d) 4.38(1H, d) 4.16(1H, brdd), 4.01(1H, dd), 2.96(1H, m), 2.54(1H, m), 2.22(1H, m). |
| 4-phenylbenzyl | CO₂H | H | CF₃ | (trans)¹H-NMR(300MHz, CDCl₃): 7.94(1H, d, J=8.7Hz), 7.18–7.65(12H, m), 6.81–6.92(2H, m), 4.53(1H, d, J=4.2Hz), 4.21(H, d, J=11.2Hz), 4.02(1H, dd, J=11 Hz, 2.5Hz), 2.78(1H, m), 2.58 (1H, m), 2.30(1H, m) |

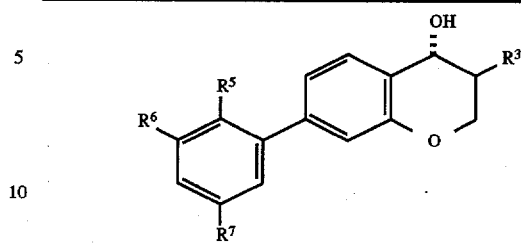

EXAMPLE 3

By saponification of the corresponding ester in accordance with Example 1J, 7-(4-hydroxy-3-carboxyphenyl)-4-hydroxy-3-phenylmethyl-2H-1-benzopyran was formed having a melting point of 158°–160° C. (cis) and 173–175° C. (trans).

EXAMPLE 4

A. 7-[(5-fluoro-(2-(4,4-dimethyl-2-oxazolinyl) phenyl]-3-phenylmethylene-1-benzopyran4-one To a stirred solution of 2-(4-fluorophenyl)-4,4-dimethyl-2- oxazoline (1.0 eq in tetrahydrofuran, 5M concentration) at −78° C. under N₂ was added n-butyllithium in hexanes (1.1 eq., 2.5M solution). The mixture was stirred at −78° C. for 1 hour, then ZnCl₂ (1M solution in ether, 1.1 eq.) was added. The mixture was warmed to 10° C. over 1 hour to give 2-(4-fluorophenyl-2-chlorozinc)4,4-diethyl-2-oxazoline (not isolated). To this solution was added 7-[((trifluoromethyl)sulfonyl)oxy]-3-phenylmethylene-1-benzopyran-4-one (1.0 eq.) and Pd (PPh₃), (0.02 eq.). The mixture was refluxed (68° C.) for 3 hours, cooled to room temperature and poured into NH₄Cl solution. The solution was extracted with 3 times diethyl ether and the combined organic fraction dried over MgSO₄. Filtration followed by solvent removal in vacuo and column chromatography (silica gel- 2:1 hexane:ether) gave the title compound as a yellow solid, 65% yield, m.p. 110°–112° C. ¹H-NMR (300 MHz, CDCl₃): 8.04 (1H, d), 7.91 (1H, s), 7.78 (1H, dd), 7.41 –7.52 (3H, m), 7.31 (2H, d), 7.06–7.18 (3H, m), 7.02 (1H, s), 5.40 (2H, s), 3.86 (2H, s), 1.31 (6H, s).

B. (3S*,4R*)7-[5-fluoro-(2-(4,4-dimethyl-2-oxazolinyl)phenyl]-4-hydroxy-3-phenylmethyl-2H-1-benzopyran To a stirred solution of the compound from step A in THF (0.1M) at 0° C. was added LiAlH₄ (1M in ether, 2.2 eq)

dropwise over 10 minutes. The mixture was warmed to room temperature and stirred for 12 hours. The mixture was cooled to 0° C., quenched with Rochelles salt, and filtered through diatomaceous earth. The aqueous layer was extracted twice with ethylacetate, and the combined organic layers were washed with brine and dried over MgSO$_4$. Filtration an solvent removal afforded a yellow oil. Chromatography over silica gel (ethylacetate:hexane) afforded a 60% yield of a white solid. M.P. 65°–70° C. (decomposed). Anal. calcd. for C$_{27}$H$_{26}$NO$_3$F: C, 75.15; H, 6.07; N, 3.25. Found: C, 74.75, H, 6.02, N, 3.09. $^1$H-NMR (300 MHz, CDCl$_3$) :7.70 (1H, dd), 7.02–7.37 (8H, m), 6.96 (1H, dd), 7.91 (1H, d), 4.51 (1H, d), 4.23 (1H, dd), 4.39 (1H, dd) 3.87 (2H, dd), 2.74 (1H, dd), 2.55 (1H, dd), 2.18–2.28 (1H, m) 1.31 (6 H, d).

C. (3S* ,4R*) 7-(2-carboxy-5-fluorophenyl)-4-, hydroxy-3-phenylmethyl-2H-1-benzopyran The compound from step B is dissolved in methyl iodide (0.5M) at room temperature and stirred for 24 hours. The methyl iodide was removed in vacuo, the oily solid was dissolved in CH$_2$Cl$_2$ and the solvent removed in vacuo. This operation was repeated to remove traces of methyl iodide. The solid was dissolved in methanol (0.5M) and 2M NaOH (0.5M) was added. The mixture was refluxed for 5 hours, cooled to room temperature and acidified to pH 2 with 1M HCl. The mixture was extracted twice with ethyl acetate, washed with brine, and dried over MgSO$_4$. Filtration and solvent removal in vacuo, followed by chromatography (silica gel, 10:1 methylene chloride:methanol) gave the desired acid, 93% yield. $^1$H-NMR (300 MHz) CD$_3$COCD$_3$): 7.80 (1H, dd), 7.48 (1H, d), 7.18 (7H, m), 7.13 (1H, dd), 6.91 (1H, dd), 6.80 (1H, d), 4.52 (1H, d), 4.23 (1H, dd), 3.96 (1H, dd), 2.89 (1H, dd), 2.54 (1H, dd), 2.19–2.30 (1H, m).

D1. (3S,4R)-7-(2-carboxy-5-fluorophenyl)-4-hydroxy-3-phenylmethyl-2H-1-benzopyran The compound from step C is dissolved in diethyl ether (0.1M) and warmed to reflux. To the solution was added dropwise S(–)methylbenzylamine (1 eq) in diethyl ether (0.1M), dropwise over 10 minutes. The mixture was cooled to room temperature and stirred for 48 hours. The precipitated salt was filtered then restirred 2 times at reflux in diethyl ether (0.1M) for 24 hours, followed by filtration. The salt (M.P.=170°–173° C.) was taken up in methylene chloride and washed 3 times with 1M HCl, then once with brine, dried over MgSO$_4$, and filtered. Solvent removal in vacuo and recrystallization (1:1-hexane:ether) gave white fine crystals, more than 99.8% enantiomeric excess by HPLC analysis. $[\alpha]_D^{25}$=+23.8, c=0.6 in CHCl$_3$. M.P.=119°–121 C. Anal. Calcd. for C$_{23}$H$_{19}$O$_4$F: c, 73.01; H, 5.06. Found: C, 72.88; H, 4.76.

D2. (3R,4S)7-(2-carboxy-5-fluorophenyl)-4-hydroxy-3-phenylmethyl-2H-1-benzopyran The filtrate from the combined salt slurries in step D1 was washed three times with 1M HCl, once with brine, and dried over MgSO$_4$. Filtration and solvent removal gave a yellow solid. A similar procedure as described in step D1 using R (+) methylbenzyl amine afforded the desired product. $[\alpha]_D^{25}$=–23.4 (c=0.6 in CHCl$_3$), M.P.=118°–120° C. Anal. Calcd. for C$_{23}$H$_{19}$O$_4$F: C, 73.01; H, 5.06. Found: C, 73.03; H, 4.84.

I claim:
1. A compound of the formula

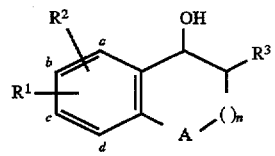

wherein
A is CH$_2$, NH or N(C$_1$–C$_6$ alkyl);
n is 1
R$^1$ is a substituent at position b or c of the formula

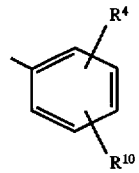

R$^2$, R$^8$, R$^9$, and R$^{10}$ are hydrogen or each independently are one or any two of the following: fluoro, chloro, C$_1$–C$_6$ alkyl, C$_1$–C$_6$ alkoxy, C$_1$–C$_4$ perfluoroalkyl, C$_1$–C$_4$ perfluoroalkoxy, C$_1$–C$_6$ alkylthio, C$_1$–C$_6$ alkylsulfinyl or C$_1$–C$_6$ alkylsulfonyl;

R$^3$ is —(CH$_2$)$_q$CHR$^{11}$R$^{12}$, —(CH$_2$)$_p$R$^{12}$,—O(CH$_2$)$_p$CHR$^{11}$R$^{12}$, or —O(CH$_2$)$_p$R$^{12}$, wherein p is 0, 1 or 2 and q is 0, 1, 2, or 3;

R$^4$ is carboxy, tetrazolyl or R$^{13}$SO$_2$NHCO;

R$^{11}$ is hydrogen, C$_1$–C$_6$ alkyl or R$^8$-substituted phenyl wherein R$^8$ is as defined above;

R$^{12}$ and R$^{13}$ are hydrogen or each independently are C$_1$–C$_6$ alkyl or C$_3$–C$_8$ cycloalkyl; or phenyl, thienyl, pyridyl, furyl, naphthyl, quinolyl, isoquinolyl, pyrimidinyl, or pyrazinyl, each of which is optionally substituted by phenyl, R$^9$, or R$^9$-substituted phenyl wherein R$^9$ is as defined above;

or a salt or esters of those compounds of formula I containing a carboxy group, wherein the esters contain ester groups selected from the group consisting of C$_1$–C$_6$ alkyl, phenyl(C$_1$–C$_6$)alkyl, C$_3$–C$_7$ cycloalkyl, and phenyl and benzyl substituted by fluoro, chloro, C$_1$–C$_6$ alkyl or C$_1$–C$_6$ alkoxy.

2. A compound according to claim 1, wherein R$^3$ is benzyl, 4-fluorobenzyl, 4-phenylbenzyl, 4-(4-fluorophenyl) benzyl, phenethyl or phenoxy.

3. A compound according to claim 1 wherein R$^2$ is hydrogen or monofluoro.

4. A compound according to claim 1 wherein R$^1$ is at position c and is 2-carboxyphenyl, 2-carboxy-5-chlorophenyl, 2-carboxy-4-chlorophenyl, 2-carboxy-3-fluorophenyl, 2-carboxy-5-fluorophenyl, 2-carboxy-5-trifluoromethylphenyl, 2-carboxy-4-fluorophenyl, 2-carboxy-6-fluorophenyl, 2-tetrazolyl-5-fluorophenyl or 3-carboxyphenyl.

5. A compound according to claim 1 wherein R$^3$ and the adjacent hydroxy group are trans.

6. A compound according to claim 5 wherein R$^1$ is 2-carboxy-5-fluorophenyl, R$^2$ is hydrogen, and R$^3$ is benzyl.

7. A compound according to claim 6 wherein the absolute stereochemistry at the position to which R$^3$ is joined is S and at the position to which the hydroxy group is joined is R.

8. A compound according to claim 6 wherein the absolute stereochemistry at the position to which R$^3$ is joined is R and at the position to which the hydroxy group is joined is S.

9. A compound according to claim 5 wherein $R^1$ is 2-carboxy-5-fluorophenyl or 2-carboxy-4-chlorophenyl, $R^2$ is hydrogen, and $R^3$ is 4-phenylbenzyl.

10. A compound according to claim 1 wherein A is $CH_2$, $R^3$ is 4-phenylphenoxy, and $R^1$ is 2-carboxy-5-fluorophenyl.

11. A pharmaceutical composition for the treatment of $LTB_4$ induced illnesses which comprises a compound of formula I as defined in claim 1 in a mixture with a pharmaceutical carrier.

12. A method for the receptor binding inhibition of $LTB_4$ which comprises administering to a subject in need of such inhibition an effective amount of a compound of formula I according to claim 1.

13. A process for preparing a compound of the formula

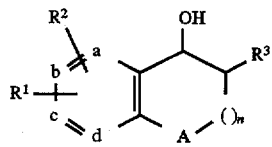　　　　I wherein

A is $CH_2NH$ or $N(C_1-C_6)alkyl$ n is 1;

$R^1$ is a substituent at position b or c of the formula

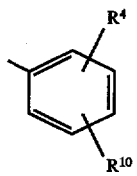

$R^1$, $R^8$, $R^9$, and $R^{10}$ are hydrogen or each independently are one or any two of the following: fluoro, chloro, $C_1-C_6$ alkyl, $C_1-C_5$ alkoxy, $C_1-C_4$ perfluoroalkyl, $C_1-C_4$ perfluoroalkoxy, $C_1-C_6$ alkylthio, $C_1-C_6$ alkylsulfinyl or $C_1-C_6$ alkylsulfonyl; $R^3$ is $—(CH_2)_qCHR^{11}R^{12}$, $—(CH_2)_qR^{12}$, $—O(CH_2)_pCHR^{11}R^{12}$, or $—O(CH_2)_pR^{12}$, wherein p is 0, 1, or 2 and q is 0, 1, 2, or 3;

$R^4$ is carboxy, tetrazolyl or $R^{13}SO_2NHCO$;

$R^{11}$ is hydrogen, $C_1-C_6$ alkyl or $R^8$-substituted phenyl wherein $R^8$ is as defined above;

$R^{12}$ and $R^{13}$ are hydrogen or each independently are $C_1-C_6$ alkyl or $C_3-C_8$ cycloalkyl; or phenyl, thienyl, pyridyl, furyl, naphthyl, quinolyl, isoquinolyl, pyrimidinyl, or pyrazinyl, each of which is optionally substituted by phenyl, $R^9$, or $R^9$-substituted phenyl wherein $R^1$ is as defined above;

or a salt or ester of those compounds of formula I containing a carboxy group, wherein the esters contain ester groups selected from the group consisting of $C_1-C_6$ alkyl, phenyl($C_1-C_6$)alkyl, $C_3-C_7$ cycloalkyl, and phenyl and benzyl substituted by fluoro, chloro, $C_1-C_6$ alkyl or $C_1-C_6$ alkoxy, by reducing a compound of the formula

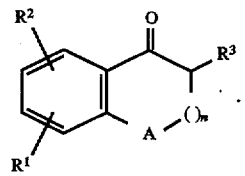　　　　XIII

* * * * *